United States Patent
Totani et al.

(10) Patent No.: US 12,305,194 B2
(45) Date of Patent: May 20, 2025

(54) CELL CULTURE METHOD AND CELL CULTURE SYSTEM

(71) Applicant: TOYO SEIKAN GROUP HOLDINGS, LTD., Tokyo (JP)

(72) Inventors: Takahiko Totani, Yokohama (JP); Yousuke Matsuoka, Yokohama (JP); Satoshi Tanaka, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 229 days.

(21) Appl. No.: 16/486,212

(22) PCT Filed: Jan. 25, 2018

(86) PCT No.: PCT/JP2018/002317
§ 371 (c)(1),
(2) Date: Aug. 15, 2019

(87) PCT Pub. No.: WO2018/150841
PCT Pub. Date: Aug. 23, 2018

(65) Prior Publication Data
US 2020/0056148 A1   Feb. 20, 2020

(30) Foreign Application Priority Data
Feb. 20, 2017   (JP) ................... 2017-029163

(51) Int. Cl.
*C12N 5/0735*   (2010.01)
*C12N 5/074*   (2010.01)

(52) U.S. Cl.
CPC .......... *C12N 5/0606* (2013.01); *C12N 5/0696* (2013.01); *C12N 2500/30* (2013.01); *C12N 2533/52* (2013.01); *C12N 2533/90* (2013.01)

(58) Field of Classification Search
CPC ............... C12N 5/0606; C12N 5/0696; C12N 2500/30; C12N 2533/52; C12N 2533/90; C12N 1/00; C12N 5/00; C12N 2533/30; C12M 1/00; C12M 3/00; C12M 23/20
See application file for complete search history.

(56) References Cited

U.S. PATENT DOCUMENTS

| | | | |
|---|---|---|---|
| 10,066,203 B2 | 9/2018 | Fryer et al. | |
| 2003/0017142 A1* | 1/2003 | Toner ................. | A61M 1/3472 435/370 |
| 2006/0263878 A1* | 11/2006 | Mochitate ............. | B82Y 30/00 435/366 |
| 2007/0275365 A1 | 11/2007 | Lui | |
| 2009/0215177 A1 | 8/2009 | Fryer et al. | |
| 2009/0269848 A1 | 10/2009 | Miyazaki et al. | |
| 2010/0087002 A1 | 4/2010 | Fryer | |
| 2010/0129910 A1 | 5/2010 | Evseenko et al. | |
| 2010/0323165 A1* | 12/2010 | Sakuma ................ | B05D 3/067 428/167 |
| 2011/0117645 A1 | 5/2011 | Yasuda et al. | |
| 2014/0127806 A1 | 5/2014 | Sekiguchi et al. | |
| 2016/0052994 A1 | 2/2016 | Sekiguchi et al. | |
| 2017/0319665 A1 | 11/2017 | Koizumi et al. | |
| 2018/0201898 A1 | 7/2018 | Takahashi et al. | |
| 2018/0334656 A1* | 11/2018 | Suemori ............. | C12N 5/0606 |

FOREIGN PATENT DOCUMENTS

| | | | | |
|---|---|---|---|---|
| JP | H044869 A | * | 1/1992 | |
| JP | 2007-508015 A | | 4/2007 | |
| JP | 2015-178526 A | | 10/2015 | |
| JP | 5790056 B2 | * | 10/2015 | ............ C12M 23/02 |
| JP | 2015-216913 A | | 12/2015 | |
| KR | 10-2017-0001727 A | | 1/2017 | |
| WO | 2007/023875 A1 | | 3/2007 | |
| WO | 2009/123349 A1 | | 10/2009 | |
| WO | 2014/103534 A1 | | 7/2014 | |
| WO | 2016/067629 A1 | | 5/2016 | |
| WO | 2016/136251 A1 | | 9/2016 | |
| WO | 2017/082220 A1 | | 5/2017 | |

OTHER PUBLICATIONS

Communication dated Jan. 21, 2021 from the Korean Intellectual Property Office in Application No. 10-2019-7022645.
Takamichi Miyazaki et al., "Efficient Adhesion Culture of Human Pluripotent Stem Cells Using Laminin Fragments in an Uncoated Manner", Scientific Reports, Jan. 30, 2017, vol. 7:41165, pp. 1-8 (8 pages).
Communication issued Jul. 24, 2020 by the Korean Patent Office in corresponding application No. 10-2019-7022645.
Written Opinion in International Application No. PCT/JP2018/002317, issued on May 1, 2018.
International Preliminary Report on Patentability with a Translation of Written Opinion in International Application No. PCT/JP2018/002317, issued on Aug. 29, 2019.

(Continued)

*Primary Examiner* — Titilayo Moloye
(74) *Attorney, Agent, or Firm* — Sughrue Mion, PLLC

(57) ABSTRACT

A cell culture method and a cell culture system, wherein: at least a part of a culture surface of a culture container is formed of a base material, the base material having a contact angle of not more than 84°, being selected from polyethylene, polypropylene, polymethylpentene, cyclic olefin polymer, cyclic olefin copolymer, polyvinyl chloride, polyurethane, methyl polymethacrylate, polyester, polyamide, ionomer, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer and the like, and having been irradiated or hydrophilized; a medium containing laminin or a fragment thereof as a cell adhesion factor and cells are accommodated in the culture container; and adherent cells are thus cultured so that the adherent cells can be preferably cultured without coating the culture container with laminin.

6 Claims, 10 Drawing Sheets

(56) References Cited

OTHER PUBLICATIONS

International Search Report on International Application No. PCT/JP2018/002317, issued on May 1, 2018.
Yasushi Tamada et al., "Fibroblast growth on polymer surfaces and biosynthesis of collagen", Journal of Biomedical Materials Research, 1994, vol. 28, pp. 783-789 (7 pages total).
Scott E. Baker et al., "Morphogenetic Effects of Soluble Laminin-5 on Cultured Epithelial Cells and Tissue Explants", Experimental Cell Research, 1996, vol. 228, No. 0325, pp. 262-270 (9 pages total).
Extended European Search Report issued Oct. 22, 2020 in corresponding European Application No. 18754360.8.
Ryan, "Evolution of Cell Culture Surfaces", BioFiles, Jan. 1, 2008, https://www.sigmaaldrich.com/technical-documents/articles/biofiles/evolution-of-cell.html (4 pages total).
Gotoh et al., "Wettability characteristics of poly(ethylene terephthalate) films treated by atmospheric pressure plasma and ultraviolet excimer light", Polymer Journal, 2011, vol. 43, No. 6, pp. 545-551 (7 pages total).
Toshio Ogawa, et al., "Effect of Humidity in Corona Discharge Treatment on Adhesive Strength of Polyethylene Sheet", Journal of the Adhesion Society of Japan, vol. 36, No. 11 (2000).

\* cited by examiner

Fig. 4

| | Material | Electron beam (kGy) | Excimer (mm/sec) | Corona (times) | Contact angle (°) | Culture days | Cell adhesion |
|---|---|---|---|---|---|---|---|
| Comparative Example 1 | PE | 25 | — | — | 96.7 | 1 day | Poor |
| Comparative Example 2 | PE | — | 40 | — | 90.0 | 1 day | Poor |
| Comparative Example 3 | COC | 25 | — | — | 89.5 | 1 day | Poor |
| Comparative Example 4 | PET | — | — | — | 70.8 | 1 day | Poor |
| Example 1 | PE | — | 8 | — | 84.0 | 1 day | Good |
| Example 2 | PE | — | 5 | — | 82.0 | 7 days | Good |
| Example 3 | PE | — | — | 1 | 65.0 | 1 day | Good |
| Example 4 | PE | — | — | 3 | 51.0 | 6 days | Good |
| Example 5 | PET | 10 | — | — | 72.8 | 7 days | Good |
| Example 6 | PET | 18 | — | — | 71.0 | 1 day | Good |
| Example 7 | PET | 18 | — | 1 | 57.3 | 1 day | Good |
| Example 8 | PET | 18 | — | 3 | 47.8 | 1 day | Good |
| Example 9 | COC | — | — | 3 | 65.9 | 7 days | Good |

Fig. 5

| | Material | Electron beam (kGy) | Excimer (nm/sec) | Corona (times) | Contact angle (°) | Culture days | Cell adhesion Laminin 0.125 μg/cm² | Cell adhesion Laminin 0.5 μg/cm² | Cell adhesion Laminin 4.0 μg/cm² |
|---|---|---|---|---|---|---|---|---|---|
| Example 10 | PE | 25 | 2 | - | 64.0 | 7 days | Good | Good | Good |
| Example 11 | PET | 38 | - | - | 52.7 | 7 days | Good | Good | Good |

Fig. 10

CELL CULTURE METHOD AND CELL CULTURE SYSTEM

CROSS REFERENCE TO RELATED APPLICATIONS

This application is a National Stage of International Application No. PCT/JP2018/002317 filed Jan. 25, 2018, claiming priority based on Japanese Patent Application No. 2017-029163 filed Feb. 20, 2017.

TECHNICAL FIELD

The present invention relates to a cell culture technology, particularly, a cell culture method and a cell culture system for adhering cells to a culture container to culture the cells.

BACKGROUND ART

In recent years, a cell, a tissue, a microorganism and the like have been required to be efficiently cultured in mass under an artificial environment in fields such as production of a medicine, gene therapy, regenerative medicine and immunotherapy.

Under such a situation, the cells and a medium are injected into a culture container to culture the cells.

In general, when adhesion culture of pluripotent stem cells (iFS cells or the like) or embryonic stem cells (ES cells) is conducted in the culture container, pretreatment for coating a culture surface of the culture container with a cell adhesion factor such as laminin is required (see Patent Document 1). Specifically, for example, a laminin solution is put in the culture container and left to stand at 37° C. for 1 hour or more to coat the culture container with laminin, and then the laminin solution is removed from the culture container, the cells and the medium have been put in the culture container to conduct adhesion culture of the cells.

RELATED ART DOCUMENTS

Patent Documents

Patent Document 1: JP-A-2015-178526

SUMMARY OF THE INVENTION

Problems to be Solved by the Invention

However, a problem of complication has remained in requiring coating of a culture container with laminin in order to thus conduct adhesion culture of cells. Moreover, when the culture container coated with laminin is supplied, a problem of tough work of production and quality control has remained, Accordingly, the present inventors have made research on whether or not cells can be adhered to a culture container and cultured therein by mixing laminin in a medium without coating the culture container with laminin.

As a result, when a culture container composed of a hydrophobic material is used, even if laminin is mixed in the medium to culture cells, the cells have been unable to be adhered to the culture container and cultured. The reason is assumed as described below.

As shown in FIG. 1, the medium contains miscellaneous proteins, and a culture surface of the culture container is formed in a state of being covered with proteins such as albumin. At this time, when the culture surface is composed of a hydrophilic material, it is considered that laminin and albumin or the like causes exchange adsorption to the culture surface, whereby the culture surface is coated with laminin. On the other hand, when the culture surface is composed of the hydrophobic material, it is considered that albumin or the like causes hydrophobic bonding to the culture surface, and therefore cannot cause the exchange adsorption with laminin, whereby the culture surface has been unable to be coated with laminin.

Here, the invention according to Patent Document 1 describes that a culture container is coated with laminin, and also that cells are cultured by using a medium to which laminin is added.

However, nothing is indicated on a specific configuration for achieving the art, and nothing has been examined on capability of culturing the cells by using the medium to which laminin is added by using a culture container having what kind of characteristics.

The present invention has been made in view of the above-described circumstances, and an objective of the present invention is to provide a cell culture method and a cell culture system in which adherent cells can be preferably cultured without coating a culture container with laminin.

Means for Solving the Problems

In order to achieve the above-described objective, a cell culture method of the present invention is a cell culture method for adhering cells to a culture container to culture the cells, which is configured in such a manner that: at least a part of a culture surface of the culture container is formed of a base material, the base material having a contact angle of not more than 84°, being selected from a group consisting of polyethylene, polypropylene, polymethylpentene, a cyclic olefin polymer, a cyclic olefin copolymer, polyvinyl chloride, polyurethane, polyester, polyamide, an ionomer, an ethylene-vinyl acetate copolymer, an ethylene-vinyl alcohol copolymer, an ethylene-acrylic acid copolymer, an ethylene-methyl acrylate copolymer, an ethylene-methacrylic acid copolymer, an ethylene-methyl methacrylate copolymer, polyacrylic acid, polymethacrylic acid, methyl polyacrylate, methyl polymethacrylate, polydimethylsiloxane and a fluorine-based resin, and having been irradiated or hydrophilized; and a medium containing laminin or a fragment thereof as a cell adhesion factor and the cells are housed in the culture container, and the cells are thus cultured.

Moreover, a cell culture system of the present invention is a cell culture system for adhering cells to a culture container to culture the cells, which is configured in such a manner that the cell culture system comprises: a culture container in which at least a part of a culture surface of the culture container is formed of a base material, the base material having a contact angle of not more than 84°, being selected from a group consisting of polyethylene, polypropylene, polymethylpentene, a cyclic olefin polymer, a cyclic olefin copolymer, polyvinyl chloride, polyurethane, polyester, polyamide, an ionomer, an ethylene-vinyl acetate copolymer, an ethylene-vinyl alcohol copolymer, an ethylene-acrylic acid copolymer, an ethylene-methyl acrylate copolymer, an ethylene-methacrylic acid copolymer, an ethylene-methyl methacrylate copolymer, polyacrylic acid, polymethacrylic acid, methyl polyacrylate, methyl polymethacrylate, polydimethylsiloxane and a fluorine-based resin, and having been irradiated or hydrophilized; and a medium container in which the medium containing laminin or the fragment thereof as a cell adhesion factor is housed, wherein the medium is transferred from the medium container to the culture container, and the cells are injected into the culture container, and the cells are thus cultured.

Moreover, a cell culture system of the present invention is a cell culture system for adhering cells to a culture container to culture the cells, which is configured in such a manner that the cell culture system comprises: a culture container in which at least a part of a culture surface of the culture container is formed of a base material, the base material having a contact angle of not more than 84°, being selected from a group consisting of polyethylene, polypropylene, polymethylpentene, a cyclic olefin polymer, a cyclic olefin copolymer, polyvinyl chloride, polyurethane, polyester, polyamide, an ionomer, an ethylene-vinyl acetate copolymer, an ethylene-vinyl alcohol copolymer, an ethylene-acrylic acid copolymer, an ethylene-methyl acrylate copolymer, an ethylene-methacrylic acid copolymer, an ethylene-methyl methacrylate copolymer, polyacrylic acid, polymethacrylic acid, methyl polyacrylate, methyl polymethacrylate, polydimethylsiloxane and a fluorine-based resin, and having been irradiated or hydrophilized; a medium container in which a medium is housed; and a laminin supply container in which laminin or a fragment thereof as a cell adhesion factor is housed, wherein the medium is transferred from the medium container to the culture container, the cells are injected into the culture container, and the laminin or the fragment thereof is transferred from the laminin supply container to the culture container, and the cells are thus cultured.

Advantageous Effects of the Invention

The present invention can provide a cell culture method and a cell culture system in which adherent cells can be preferably cultured without coating a culture container with laminin.

BRIEF DESCRIPTION OF THE DRAWINGS

FIG. 4 is a diagram showing the results of treatment conditions, a contact angle, culture days and cell adhesion on a culture surface of the culture containers in Comparative Examples 1 to 4 and Examples 1 to 9.

FIG. 5 is a diagram showing the results of treatment conditions, a contact angle, culture days and cell adhesion on a culture surface of the culture containers in Examples 10 to 11.

Figure 10:
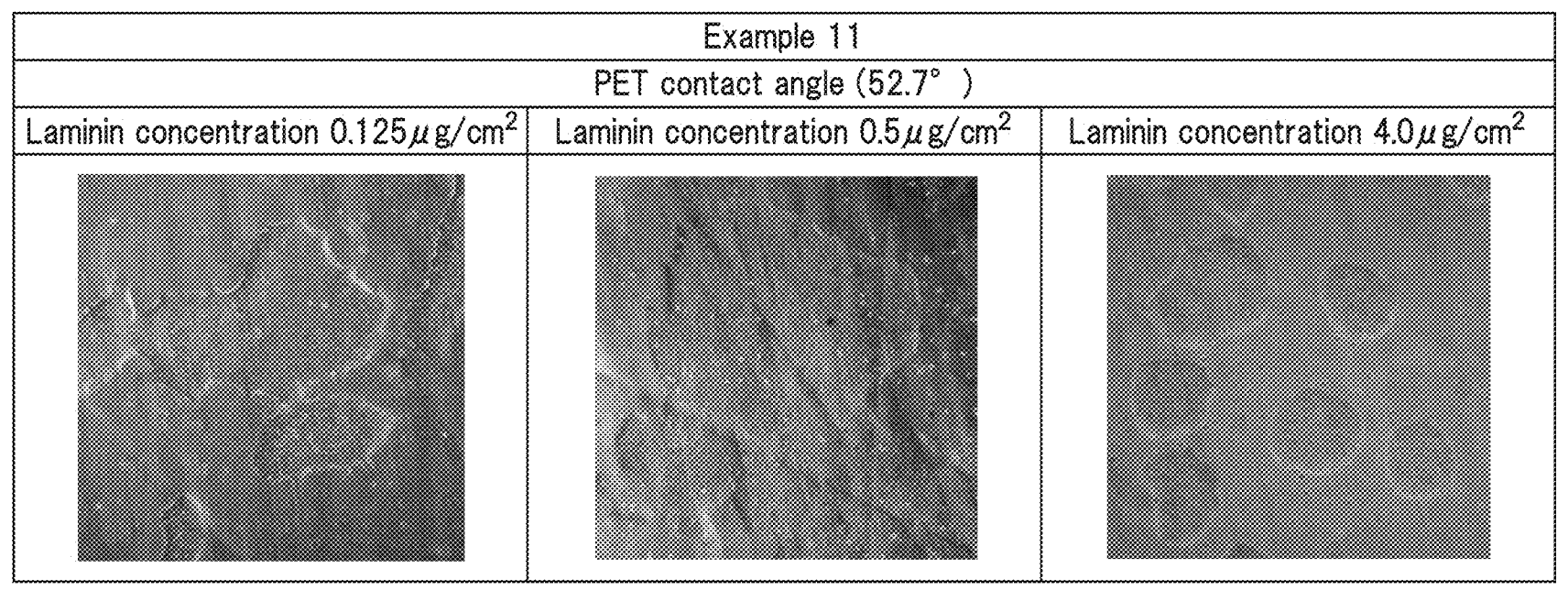

FIG. 10 is a diagram showing a photomicrograph of culture results (state of a culture surface) by using the culture container in Example 11.

EMBODIMENTS FOR CARRYING OUT THE INVENTION

Figure 1:
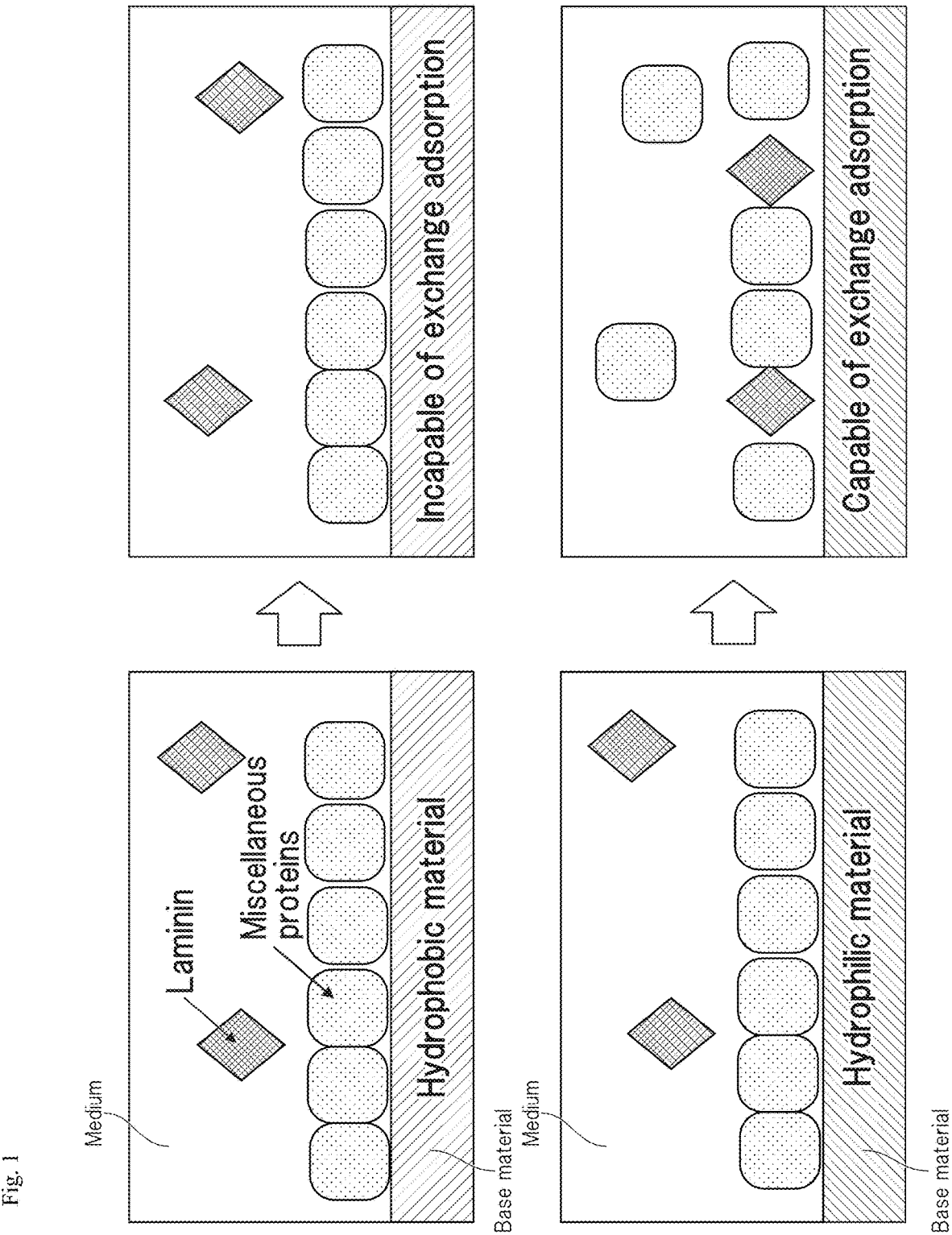
FIG. 1 is an explanatory drawing showing a reason why a cell culture method of the present invention cannot be applied to a culture container having a hydrophobic culture surface.

Hereinafter, an embodiment of a cell culture method and a cell culture system of the present invention will be described in detail.

The cell culture method of the present embodiment is a cell culture method for adhering cells to a culture container to culture the cells, which is characterized in that: at least a part of a culture surface of the culture container is formed of a base material, the base material having a contact angle of not more than 84°, being selected from a group comprising polyethylene, polypropylene, polymethylpentene, cyclic olefin polymer, cyclic olefin copolymer, polyvinyl chloride, polyurethane, polyester, polyamide, ionomer, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer, polyacrylic acid, polymethacrylic acid, methyl polyacrylate, methyl polymethacrylate, polydimethylsiloxane and fluorine-based resin, and having been irradiated or hydrophilized; and the medium containing laminin or the fragment thereof as a cell adhesion factor and the cells are accommodated in the culture container, and the cells are thus cultured.

The term "culture surface of a culture container" means a surface in the culture container, on which the cells are adhered and cultured.

The term "contact angle" means an angle formed between a liquid surface and a solid surface in a part in which a surface of stationery liquid is in contact with a solid wall, which is also referred to as a static contact angle. The contact angle has a relationship in which surface hydrophobicity is strong when the contact angle is large, and surface hydrophilicity is strong when the contact angle is small.

In the cell culture method of the present embodiment, at least a part of the culture surface of the culture container is formed using the base material selected from the above-described various materials. Moreover, all the culture surfaces are also preferably formed using the base materials. Further, a whole of the culture container is also preferably formed using the base materials. The culture container is formed using the base materials, whereby a flexible bag-like (bag-shaped) culture container for culturing adherent cells can be preferably produced. If such a flexible bag-like culture container is used, a liquid thickness of the medium can be significantly changed in the culture container.

Moreover, in the cell culture method of the present embodiment, at least a part of the culture surface of the culture container is treated so as to have a contact angle of not more than 84°. Moreover, all the culture surfaces are also preferably treated so as to have a contact angle of not more than 84°.

Specifically, the culture surface of the culture container can be treated by using any one of hydrophilization treatment by excimer irradiation or corona treatment, or sterilization by irradiation treatment, or a combination thereof. At this time, a degree of hydrophilization can be adjusted by changing conditions such as a treatment rate in the excimer irradiation, or conditions such as the number of times of treatment in the corona treatment.

Moreover, in the irradiation treatment, any one of electron beam treatment or γ-ray treatment can be preferably used.

When the culture surface is treated so as to have a contact angle of not more than 84° by the excimer irradiation, the treatment rate is adjusted preferably to 1 to 10 mm/sec, and more preferably to 2 to 8 mm/sec at 12 V and an irradiation distance of 5 mm, for example. Moreover, when the culture surface is treated so as to have a contact angle of not more than 84° by the corona treatment, the culture surface is preferably treated about 1 to 3 times at an inter-electrode distance of 5 mm, an applied electric current of 3.5 A and a table movement speed of 5 m/min, for example.

Moreover, in the cell culture method of the present embodiment, the contact angle of the culture surface of the culture container is preferably not less than 40° and not more than 84°. The reason is that, if the contact angle is within the range thereof, the adherent cells can be more preferably adhered to the culture surface.

Here, when the culture surface of the culture container is particularly formed of polyethylene terephthalate, if the culture surface is not irradiated or hydrophilized, even if the contact angle is not more than 84°, the cells have been unable to be adhered and cultured by accommodating the medium containing laminin or the fragment thereof as the cell adhesion factor and the cells in the culture container. The reason is considered as described below.

Polyethylene terephthalate has a great number of ester bonds having polarity in a main chain skeleton, apparent hydrophilicity is improved, and the contact angle is lower than a contact angle of any other resin such as polyethylene, but a degree of freedom of a hydrophilic moiety is low, and many of the moieties are buried in a resin, and therefore polyethylene terephthalate cannot influence an adsorption reaction of albumin.

On the other hand, if polyethylene terephthalate is hydrophilized, a hydroxyl group and a carboxyl group is provided on an outermost surface, whereby a hydrophobic bond of albumin can be interfered. Moreover, if polyethylene terephthalate is irradiated, it is considered that molecular mobility is increased by cutting and cleavage of a molecular chain in the resin, and therefore a hydrophilic group can move to the outermost surface, whereby the hydrophobic bond of albumin can be interfered.

It should be noted that, as polyethylene terephthalate described in the present description and claims, polyethylene terephthalate that is commercially available as "PET" can be generally used, and specific examples thereof also include polyethylene terephthalate containing an auxiliary component such as isophthalic acid, naphthalene dicarboxylic acid, 1,4-butanediol, propylene glycol, neopentyl glycol and cyclohexanedimethanol (CHDM).

The cells to be cultured according to the cell culture method of the present embodiment are not particularly limited, as long as the cells are the adherent cells, and specific examples thereof include pluripotent stem cells (iPS cells or the like) and embryonic stem cells (ES cells).

According to the cell culture method of the present embodiment, the cells can be preferably adhered to the culture surface and cultured.

In the cell culture method of the present embodiment, as the cell adhesion factor, an adhesive protein such as fibronectin and fibrinogen can be used in addition to laminin or the fragment thereof. As the fragment of laminin, for example, laminin 511-E8 can be preferably used.

According to the cell culture method of the present embodiment, the medium containing laminin (or the fragment thereof) and the cells are accommodated in the culture container formed as described above, whereby the laminin can be adsorbed on the culture surface of the culture container.

Therefore, prior to cell culture, the cells can be adhered to the culture surface of the culture container and cultured without coating the culture surface of the culture container with laminin, and therefore conventional complicated coating of the culture container with laminin can be omitted, and simultaneously production and quality control of the culture container coated with laminin can be omitted.

The cell culture system according to the embodiment of the present invention is a cell culture system for adhering cells to a culture container to culture the cells, which is characterized in that the cell culture system comprises: a culture container in which at least a part of a culture surface of the culture container is formed of a base material, the base material having a contact angle of not more than 84°, being selected from a group comprising polyethylene, polypropylene, polymethylpentene, cyclic olefin polymer, cyclic olefin copolymer, polyvinyl chloride, polyurethane, polyester, polyamide, ionomer, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer, polyacrylic acid, polymethacrylic acid, methyl polyacrylate, methyl polymethacrylate, polydimethylsiloxane and fluorine-based resin, and having been irradiated or hydrophilized; and a medium container in which a medium containing laminin or a fragment thereof as a cell adhesion factor is accommodated, wherein the medium is transferred from the medium container to the culture container, and the cells are injected into the culture container, and the cells are thus cultured.

Figure 2:
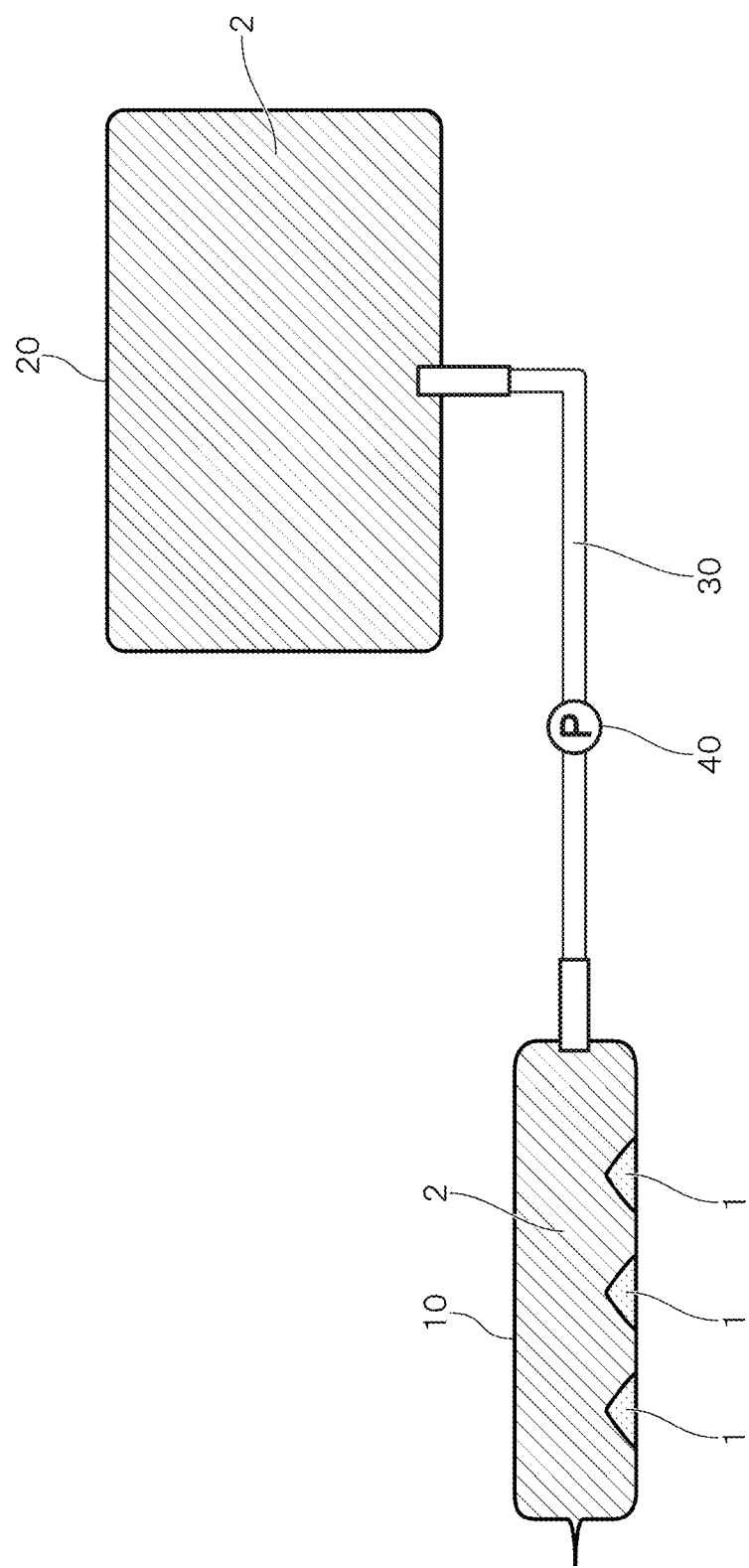
FIG. 2 is an explanatory drawing showing a schematic configuration of a cell culture system according to an embodiment of the present invention.

Specifically, for example, as schematically shown in FIG. 2, the cell culture system of the present embodiment can be configured in such a manner that a culture container 10 is connected to a medium container 20 by using a tube 30, and a pump 40 is attached to the tube 30.

Adherent cells 1 are adhered on a culture surface of the culture container 10, and cultured. The medium container 20 is filled with a laminin-containing medium 2, and the laminin-containing medium 2 is supplied to the culture container 10 through the tube 30 by driving the pump 40.

The culture surface of the culture container 10 is formed using any one of the above-described various base materials or a combination thereof, and having been hydrophilized or the like so as to have a contact angle of not more than 84°. It should be noted that only a part of the culture surface is thus formed and treated, whereby the adherent cells can also be cultured only in the part.

If the cell culture system of the present embodiment is configured in such a manner, laminin contained in the laminin-containing medium 2 transferred from the medium container 20 to the culture container 10 can be adsorbed on the culture surface of the culture container 10 even without coating the culture surface of the culture container 10 with laminin, and therefore the adherent cells 1 can be preferably adhered to the culture surface, and cultured.

The culture container 10 can be formed by sealing a thermoplastic resin sheet by means of heat sealing or the like, and can also be formed using various molding methods such as blow molding.

Moreover, the culture container 10 is preferably formed of a member having gas permeability. Specifically, the culture container 10 is preferably formed of a member having an oxygen permeability coefficient of not less than 400 mL·mm/m²·day·atm (37° C.-80% RH), and a carbon dioxide permeability coefficient of not less than 1200 mL·mm/m²·day·atm (37° C.-80% RH), is more preferably formed of a member having an oxygen permeability coefficient of not less than 1000 mL·mm/m²·day·atm (37° C.-80% RH), and a carbon dioxide permeability coefficient of not less than 3000 mL·mm/m²·day·atm (37° C.-80% RH), If the culture container 10 has such gas permeability, excellent cell growth efficiency can be obtained.

Further, the culture container 10 preferably wholly or partly has transparency so as to confirm contents. Moreover, the culture container 10 of the present embodiment is preferably formed using a flexible member.

The medium container 20 is a container that accommodates the laminin-containing medium 2 for being injected into the culture container 10. The laminin-containing medium 2 can be prepared by mixing the medium and the laminin or the fragment thereof.

In the tube 30, a material which is regularly used can be generally used, and for example, the material formed using such a material can be used as silicone rubber, soft polyvinyl chloride resin, polybutadiene resin, ethylene-vinyl acetate copolymer, chlorinated polyethylene resin, polyurethane-based thermoplastic elastomer, polyester-based thermoplastic elastomer, silicone-based thermoplastic elastomer or styrene-based elastomer such as SBS (styrene-butadiene-styrene), SIS (styrene-isoprene-styrene), SEBS (styrene-ethylene-butylene-styrene), and SEPS (styrene-ethylene-propylene-styrene). These materials are excellent in the gas permeability.

As the pump 40, a peristaltic system pump capable of transferring the laminin-containing medium 2 from the medium container 20 to the culture container 10 by drawing the tube 30 can be preferably used.

Moreover, the cell culture system according to the embodiment of the present invention is also preferably configured into a system being characterized in that, as a modified example thereof, the cell culture system comprises: a culture container in which at least a part of a culture surface of the culture container is formed of a base material, the base material having a contact angle of not more than 84°, being selected from a group comprising polyethylene, polypropylene, polymethylpentene, cyclic olefin polymer, cyclic olefin copolymer, polyvinyl chloride, polyurethane, polyester, polyamide, ionomer, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer, polyacrylic acid, polymethacrylic acid, methyl polyacrylate, methyl polymethacrylate, polydimethylsiloxane and fluorine-based resin, and having been irradiated or hydrophilized; a medium container in which a medium is accommodated; and a laminin supply container in which laminin or a fragment thereof as a cell adhesion factor is accommodated, wherein the medium is transferred from the medium container to the culture container, the cells are injected into the culture container, and the laminin or the fragment thereof is transferred from the laminin supply container to the culture container, and the cells are thus cultured.

Figure 3:
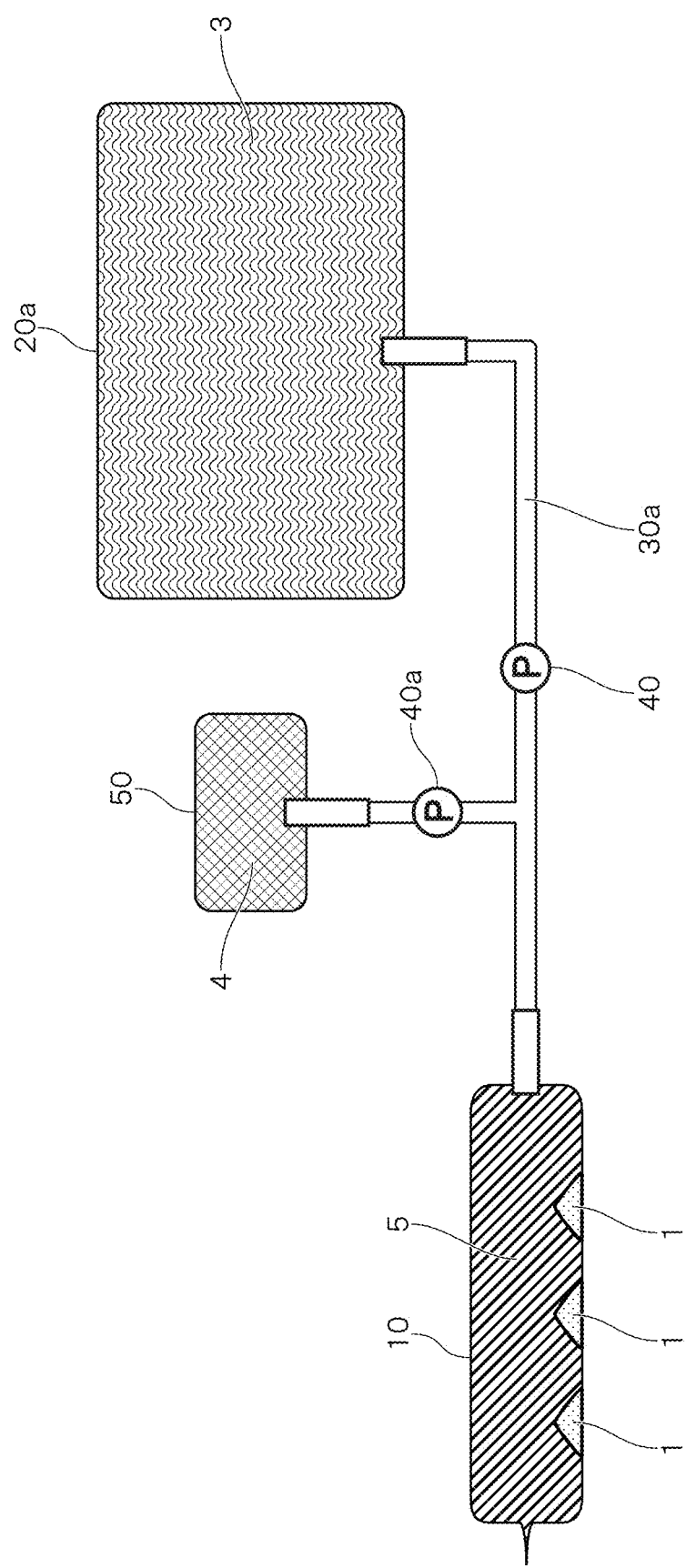
FIG. 3 is an explanatory drawing showing a schematic configuration of a modified example of a cell culture system according to an embodiment of the present invention.
Figure 6:
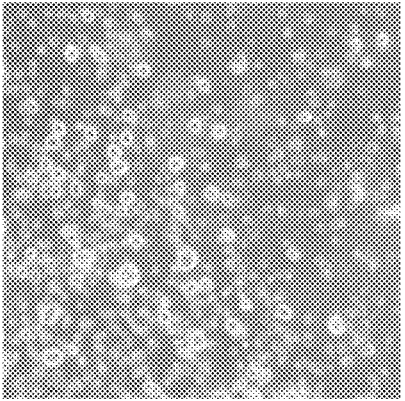
FIG. 6 is a diagram showing a photomicrograph of culture results (state of a culture surface) by using the culture containers in Comparative Examples 1 to 4.
Figure 7:
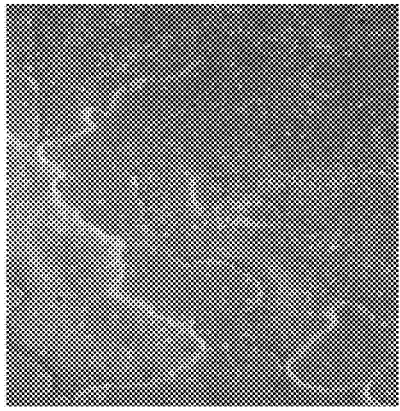
FIG. 7 is a diagram showing a photomicrograph of culture results (state of a culture surface) by using the culture containers in Examples 1 to 4.
Figure 8:
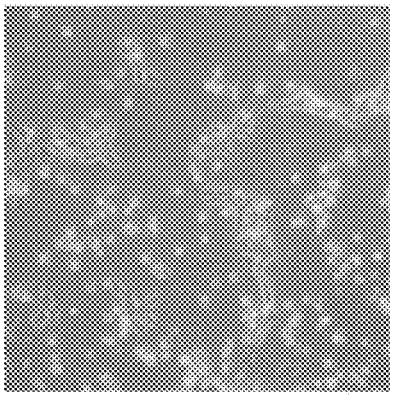
FIG. 8 is a diagram showing a photomicrograph of culture results (state of a culture surface) by using the culture containers in Examples 5 to 9.
Figure 9:
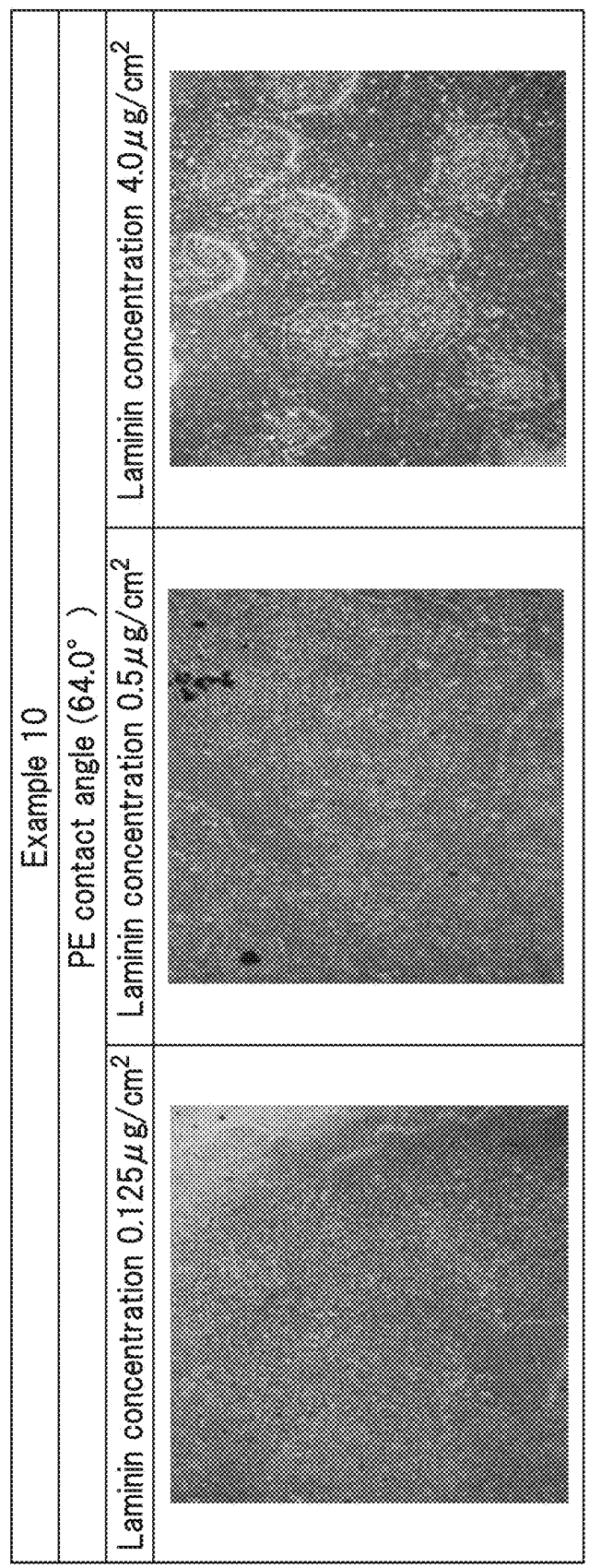
FIG. 9 is a diagram showing a photomicrograph of culture results (state of a culture surface) by using the culture container in Example 10.

Specifically, for example, as schematically shown in FIG. 3, a modified example of the cell culture system of the present embodiment can be configured in such a manner that a culture container 10 is connected to a medium container 20a and a laminin supply container 50 by using a tube 30a, and a pump 40 and a pump 40a are attached to the tube 30a.

Then, a medium 3 (containing no laminin) is transferred from the medium container 20a to the culture container 10 through the tube 30a by driving the pump 40, and laminin 4 is transferred from the laminin supply container 50 to the culture container 10 through the tube 30a by driving the pump 40a, whereby a laminin concentration adjustment medium 5 is supplied to the culture container 10.

The pump 40 and the pump 40a can be simultaneously driven. In addition thereto, when the pump 40 is driven, a branched part of the tube 30a connected to the laminin supply container 50 can be adjusted to a state of being closed by a clip or the like, and when the pump 40a is driven, the branched part of the tube 30a connected to the medium container 20a are also adjusted to the state of being closed by the clip or the like, whereby the medium 3 and the laminin 4 can be transferred, respectively. Moreover, a pump is attached to the branched part of the tube 30a connected to the culture container 10, whereby the medium 3 and the laminin 4 may be transferred by one pump, respectively.

Specifically, for example, 199 mL of the medium 3 (containing no laminin)—accommodated in the medium container 20a and 1 mL of the laminin 4 (for example, a laminin solution adjusted to a concentration of 0.1 mg/mL) accommodated in the laminin supply container 50 are transferred to the culture container 10 by pump driving, respectively, whereby the laminin concentration adjustment medium 5 having a concentration of 0.5 μg/mL can be transferred to the culture container 10. When an area of the culture surface in the culture container 10 is 200 cm², a concentration of laminin per area in a liquid thickness of 1 cm can be adjusted to be 0.5 μg/cm².

Moreover, if the liquid thickness is desired to be doubled for the reason of desirably culturing the cells at high density, although the concentration of laminin per area is not desired to be changed, 1 mL of the laminin solution adjusted to a concentration of 0.1 mg/mL and 399 mL of the medium 3 are transferred to the culture container 10, whereby such doubling can be achieved.

Further, a degree of adhesion of the cells is weakened on the way of culture in several cases. In such a case, the laminin 4 is added from the laminin supply container 50 to the culture container 10, whereby strength of adhesion of the cells can be increased.

Here, if the concentration of laminin in the laminin supply container 50 is high, a liquid amount of the laminin solution to be delivered is significantly reduced, and reduction of precision during liquid delivery by the pump driving is concerned. For example, when the concentration of laminin is desired to be adjusted to 0.5 μg/cm² in the culture container 10 having a culture area of 200 cm², the amount of laminin required is 0.1 mg. That is, when the concentration of laminin accommodated in the laminin supply container 50 is more than 0.1 mg/mL, a liquid delivery amount is less than 1 mL to be the liquid amount at which the liquid is difficult to be delivered with high precision by using a general-purpose pump.

Therefore, the concentration of laminin in the laminin supply container 50 is preferably adjusted to a level of not more than 0.1 mg/mL.

In the modified example of the cell culture method of the present embodiment, other points can be adjusted to the same conditions as in the above-described cell culture method of the present embodiment.

If the cell culture system of the present embodiment is configured as in the modified example, the medium 3 and the laminin 4 are separately transferred to the culture container 10, whereby the concentration of laminin on the culture surface of the culture container 10 can be adjusted, and a culture environment of the adherent cells 1 can be flexibly adjusted. Such performance produces an effect that cannot be obtained when a conventional culture container coated with laminin is used.

As described above, according to the cell culture method and the cell culture system of the present embodiment, the adherent cells can be preferably cultured without coating the culture container with laminin. Moreover, the concentration of laminin to be adsorbed on the culture surface of the culture container can be adjusted, and the culture environment of the adherent cells can also be flexibly adjusted.

EXAMPLES

Hereinafter, a test conducted for evaluating the present embodiment will be described. Treatment was performed to be in various values in contact angles of culture surfaces of culture containers formed using various materials, and cells were cultured by a cell culture method of the present embodiment. Specifically, the procedure is as described below.

[Culture Container]

As a culture container, a container processed into a dish shape after forming polyethylene (PE, manufactured by Ube-Maruzen Polyethylene Co., Ltd., trade name; UMERIT 125FN) into a film, a container processed into a dish shape after forming a cyclic olefin copolymer (COC, manufactured by Polyplastics Co. Ltd., trade name; TOPAS8007F-04) into a film, and a container processed into a dish shape by performing injection molding of polyethylene terephthalate (PET, manufactured by SK Chemicals Co., Ltd., trade name; BR8040) were arranged. The film of PE and COC was processed into the dish shape by folding an end of the film and welding the ends by an impulse sealer.

[Treatment of Culture Surface]

As shown in FIG. 4 and FIG. 5, each culture container, excluding a culture container in Comparative Example 4, was treated by using any one of hydrophilization treatment by an excimer irradiation device (manufactured by M.D.COM Inc.), hydrophilization treatment by a batch type corona treatment device (manufactured by KASUGA DENKI, Inc.) or electron beam treatment, or a combination thereof. The electron beam treatment was performed at a request to RADIA INDUSTRY CO., LTD.

In each treatment, a degree of hydrophilization can be adjusted by changing conditions such as a treatment rate in excimer irradiation, or conditions such as the number of times of treatment in corona treatment. The culture containers each having a culture surface having a contact angle shown in FIG. 4 and FIG. 5 were arranged by adjusting these conditions.

It should be noted that 12 V and an irradiation distance of 5 mm were applied in the excimer irradiation, and an inter-electrode distance of 5 mm, an applied electric current of 3.5 A and a table movement speed of 5 m/min were applied in the corona treatment.

[Measurement of Contact Angle]

A solid-liquid interface analysis system DropMaster 700 (manufactured by Kyowa Interface Science, Inc.) was used for measurement of the contact angle. The contact angle was measured by adding dropwise 3 μL of pure water on the film.

[Cell Culture Method]

Adherent cells used are iPS cells (1231A3 strain),

A medium used is StemFit AK02N (Catalog Number; RCAK02N, manufactured by Ajinomoto Co., Inc.).

The medium containing 10 mM of a Rho-associated kinase inhibitor; Y-27632 (Catalog Number; 253-00511, manufactured by Wako Pure Chemical Industries, Ltd.) was injected into each culture container, and simultaneously 0.5 mg/mL of laminin 511-E8 (Catalog Number; 892012, manufactured by Nippi, Inc.) was added to each culture container to be 0.5 μg/cm$^2$. Then, a cell suspension containing the iPS cells was injected thereinto, and cultured at 37° C. for 7 days. At this time, an amount of the medium was 1.5 mL, and an amount of the cell suspension was 5 μL. The number of cells disseminated was about 1.3×10$^4$ cells. Moreover, after elapse of 1 day from start of the culture, the medium was exchanged by a medium containing no Y-27632, and then the medium was exchanged every day.

[Evaluation of Adhesion]

An adhesion state of the cells after 1 day, 6 days or 7 days from culture was observed with a microscope, and adhesion of the cells was evaluated based on whether or not adhesion and extension of the cells can be observed.

It should be noted that the cells are adhered thereto in 1 day when suitable treatment capable of culturing the adherent cells is performed on the culture surface in the culture container. Moreover, when the cells are not adhered thereto in 1 day, the cells are not adhered thereto even after elapse of subsequent days, and therefore in Comparative Examples 1 to 4, culture suitability (propriety of cell adhesion) of each culture container was judged only after 1 day from culture.

[Influence of Concentration of Laminin]

Cell culture was performed according to the procedure described above except that laminin 511-E8 was added to each culture container to be 0.125 μg/cm$^2$, 0.5 μg/cm$^2$ and 4.0 μg/cm$^2$, respectively, in a concentration of laminin.

The results of the cell culture performed as described above were shown in FIG. 4 and FIG. 5, in which a case where adhesion culture of the cells was able to be performed was shown as good, and a case where the adhesion culture of the cells was unable to be performed was shown as poor. Moreover, a photomicrograph obtained by picking up a state of the culture surface was shown in FIGS. 6 to 10.

In Comparative Examples 1 to 3, in the culture container formed of polyethylene (PE) or a cyclic olefin copolymer (COC), and having a culture surface having a contact angle of more than 84°, the adherent cells were unable to be appropriately cultured. Moreover, in Comparative Example 4, in the culture container formed of polyethylene terephthalate, and having been neither irradiated nor hydrophilized, the adherent cells were unable to be appropriately cultured.

By contrast, in Examples 1 to 9, in the culture container formed of polyethylene (PE), polyethylene terephthalate (PET) or a cyclic olefin copolymer (COC), having a culture surface having a contact angle of not more than 84°, and having been irradiated or hydrophilized, the adherent cells were able to be cultured.

Moreover, in Examples 10 and 11, in the culture container formed of polyethylene (PE) or polyethylene terephthalate (PET), having a culture surface having an contact angle of not more than 84°, and having been irradiated or hydrophilized, the adherent cells were able to be cultured in any case where the concentration of laminin was 0.125 μg/cm$^2$, 0.5 μg/cm$^2$ or 4.0 μg/cm$^2$.

It should be appreciated that the present invention is not limited to the embodiments or Examples described above, and various modifications can be obviously made within the scope of the present invention.

For example, although the iPS cells are used as the adherent cells in Examples described above, the adherent cells are not limited thereto, and other cells can be used, as long as the cells are the adherent cells. Moreover, a kind or the like of the medium can also be appropriately changed.

The entire contents of Document described in the description and the description of the Japanese application serving as a basis of claiming the priority concerning the present application to the Paris Convention are incorporated by reference herein.

INDUSTRIAL APPLICABILITY

The present invention can be preferably utilized when adherent cells are cultured in mass by using a culture container.

EXPLANATION OF NUMERICAL SYMBOLS

1 Adherent cell
2 Laminin-containing medium
3 Medium (containing no laminin)
4 Laminin
5 Laminin concentration adjustment medium
10 Culture container
20, 20a Medium container
30, 30a Tube
40, 40a Pump
50 Laminin supply container

The invention claimed is:

1. A cell culture method for adhering cells to a culture container to culture the cells, comprising:
arranging the culture container, wherein at least a part of a culture surface of the culture container is formed of a base material that is any one of polyethylene, cyclic olefin copolymer or polyethylene terephthalate, wherein at least the part of the culture surface is treated using hydrophilization treatment by corona treatment to have a contact angle of not less than 51.0° and not more than 84.0°, and wherein the culture surface is not pre-coated with laminin, and wherein the culture surface is exposed to a medium;
accommodating the medium and the cells in the culture container, wherein the medium comprises laminin or a fragment thereof as a cell adhesion factor; and
culturing the cells so as to absorb the cell adhesion factor on the treated culture surface and adhere the cells to the culture surface which has adsorbed the cell adhesion factor.

2. The cell culture method according to claim 1, wherein the cells are pluripotent stem cells, embryonic stem cells or differentiated cells thereof.

3. The cell culture method according to claim 1, wherein the cells are cultured in a closed system by using the culture container.

4. A cell culture system for adhering cells to a culture container to culture the cells, comprising:
a culture container, wherein at least a part of a culture surface of the culture container is formed of a base material that is any one of polyethylene, cyclic olefin copolymer or polyethylene terephthalate, wherein at least the part of the culture surface has a contact angle of not less than 51.0° and not more than 84.0° using hydrophilization treatment by corona treatment and without coating the culture surface with laminin, and wherein the culture surface is exposed to a medium; and
a medium container accommodating the medium, wherein the medium comprises laminin or a fragment thereof as a cell adhesion factor,
wherein the cell culture system is configured such that the medium is transferred from the medium container to the culture container, the cells are injected into the culture container, and the cells are thus cultured so as to absorb the cell adhesion factor on the treated culture surface and adhere the cells to the culture surface which has adsorbed the cell adhesion factor.

5. A cell culture system for adhering cells to a culture container to culture the cells, comprising:
a culture container, wherein at least a part of a culture surface of the culture container is formed of a base material that is any one of polyethylene, cyclic olefin copolymer or polyethylene terephthalate, wherein at least the part of the culture surface has a contact angle of not less than 51.0° and not more than 84.0° using hydrophilization treatment by corona treatment without coating the culture surface with laminin, and wherein the culture surface is exposed to a medium;
a medium container accommodating the medium; and
a laminin supply container accommodating laminin or a fragment thereof as a cell adhesion factor,
wherein the cell culture system is configured such that the medium is transferred from the medium container to the culture container, the cells are injected into the culture container, the cell adhesion factor is transferred from the laminin supply container to the culture container, and the cells are thus cultured so as to absorb the cell adhesion factor on the treated culture surface and adhere the cells to the culture surface which has adsorbed the cell adhesion factor.

6. The cell culture system according to claim 5, wherein a concentration of laminin accommodated in the laminin supply container is not more than 0.1 mg/mL.

* * * * *